(12) United States Patent
Noda (10) Patent No.: US 11,681,778 B2
(45) Date of Patent: Jun. 20, 2023

(54) ANALYSIS DATA PROCESSING METHOD AND ANALYSIS DATA PROCESSING DEVICE

(71) Applicant: SHIMADZU CORPORATION, Kyoto (JP)

(72) Inventor: Akira Noda, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 328 days.

(21) Appl. No.: 16/322,338

(22) PCT Filed: Aug. 3, 2016

(86) PCT No.: PCT/JP2016/072873
§ 371 (c)(1),
(2) Date: Jan. 31, 2019

(87) PCT Pub. No.: WO2018/025361
PCT Pub. Date: Feb. 8, 2018

(65) Prior Publication Data
US 2019/0179874 A1    Jun. 13, 2019

(51) Int. Cl.
*G06F 17/18* (2006.01)
*G06N 99/00* (2019.01)
(Continued)

(52) U.S. Cl.
CPC ............. *G06F 17/18* (2013.01); *G01N 21/00* (2013.01); *G01N 21/35* (2013.01); *G01N 23/223* (2013.01);
(Continued)

(58) Field of Classification Search
CPC ........ G06F 17/18; G16B 40/00; G01N 21/00; G01N 21/35; G01N 23/223; G01N 27/62;
(Continued)

(56) References Cited

U.S. PATENT DOCUMENTS

| 5,228,113 A | * | 7/1993 | Shelton .................. G06N 3/084 706/25 |
| 8,378,296 B1 | * | 2/2013 | Enke ..................... H01J 49/025 250/288 |

(Continued)

OTHER PUBLICATIONS

Communication dated Jun. 2, 2020, from The State Intellectual Property Office of the P.R. of China in Application No. 201680088305.X.

(Continued)

*Primary Examiner* — Alexander Satanovsky
*Assistant Examiner* — Lyudmila Zaykova-Feldman
(74) *Attorney, Agent, or Firm* — Sughrue Mion, PLLC (57) ABSTRACT

An analysis data processing method for processing analysis data collected with an analyzing device for each of a plurality of samples, by applying an analytical technique using statistical machine learning to multidimensional analysis data formed by output values obtained from a plurality of channels of a multichannel detector provided in the analyzing device, the method including: acquiring a non-linear regression or non-linear discrimination function expressing analysis data obtained for known samples; calculating a contribution value of each of the output values obtained from the plurality of channels forming the analysis data of the known samples, to the acquired non-linear regression or non-linear discrimination function, based on a differential value of the non-linear regression function or non-linear discrimination function; and identifying one or more of the plurality of channels of the detector, which are to be used for processing analysis data obtained for an unknown sample, based on the contribution value.

12 Claims, 3 Drawing Sheets

(51) Int. Cl.

| | | |
|---|---|---|
| *G01N 30/78* | (2006.01) | |
| *G01N 21/00* | (2006.01) | |
| *G16B 40/00* | (2019.01) | |
| *G16B 40/30* | (2019.01) | |
| *G01N 21/35* | (2014.01) | |
| *G01N 23/223* | (2006.01) | |
| *G01N 27/62* | (2021.01) | |
| *G01N 30/86* | (2006.01) | |
| *G01N 33/44* | (2006.01) | |
| *G01N 33/48* | (2006.01) | |
| *G06N 3/08* | (2023.01) | |

(52) U.S. Cl.
CPC ............. *G01N 27/62* (2013.01); *G01N 30/78* (2013.01); *G01N 30/8675* (2013.01); *G01N 33/442* (2013.01); *G01N 33/48* (2013.01); *G06N 3/08* (2013.01); *G06N 99/00* (2013.01); *G16B 40/00* (2019.02); *G16B 40/30* (2019.02)

(58) Field of Classification Search
CPC .. G01N 30/78; G01N 30/8675; G01N 33/442; G01N 33/48; G06N 3/08; G06N 99/00
See application file for complete search history.

(56) References Cited

U.S. PATENT DOCUMENTS

| | | | | |
|---|---|---|---|---|
| 10,515,312 B1 * | 12/2019 | Kubo | ................... | G06N 3/084 |
| 2004/0159783 A1 * | 8/2004 | Gavin | ................. | H01J 49/0036 |
| | | | | 250/282 |
| 2008/0016102 A1 * | 1/2008 | Albornoz | .............. | G06F 16/907 |
| | | | | 707/999.102 |
| 2010/0211545 A1 * | 8/2010 | Soni | ........................ | G06F 16/27 |
| | | | | 707/623 |
| 2012/0089344 A1 * | 4/2012 | Wright | ................. | G06K 9/0053 |
| | | | | 703/2 |
| 2013/0267796 A1 | 10/2013 | Moreno | | |
| 2019/0103259 A1 * | 4/2019 | McIntosh | .............. | H01J 49/165 |

OTHER PUBLICATIONS

G. Ball et al., " An integrated approach utilizing artificial neural networks and SELDI mass spectrometry for the classification of human tumours and rapid identification of potential biomarkers", Bioinformatics, Dec. 31, 2002, vol. 18, No. 3, pp. 395-404 (10 pages total).

Communication dated Jun. 26, 2019, from the European Patent Office in counterpart European Application No. 16911620.9.

Tom Howley, et al., "The effect of principal component analysis on machine learning accuracy with highdimensional spectral data", Knowledge-Based Systems, Elsevier, Amsterdam, NL, Sep. 1, 2006, vol. 19, No. 5, pp. 363-370, XP027934171 (8 pages total).

Tahenryou Kaiseki (Shuseibun Bunseki) Wo Katsuyou Shita Kuromatodeeta Kaiseki, "Chromatographic data analysis using multivariate analysis (principal component analysis))", Shimadzu Corporation Website, [accessed on Jul. 25, 2016], the Internet, 4 pages.

Ngoc-Diep Ho, "Nonnegative matrix factorization algorithms and applications", Research Gate, the Internet, Jun. 2008, 186 pages.

Tomoo Aoyama et al., "Obtaining the Correlation Indices between Drug Activity and Structural Parameters Using a Neural Network", Chem. Pharm. Bull., Feb. 1991, pp. 372-378, vol. 39, No. 2.

Karen Simonyan et al., "Deep Inside Convolutional Networks: Visualising Image Classification Models and Saliency Maps", the Internet, Apr. 19, 2014, 8 pages.

Tadashi Goto et al., "Non-Linear Modeling of Water Content in Processed Green Tea Using ANN and PCA", Application of the Hyphenated PCA-ANN regression Model to the Absorbance Obtained by NIRS, 1999, pp. 127-136, vol. 61, Issue 2.

International Search Report for PCT/JP2016/072873 dated Nov. 8, 2016 [PCT/ISA/210].

Written Opinion for PCT/JP2016/072873 dated Nov. 8, 2016 [PCT/ISA/237].

First Office Action dated May 6, 2022 from the European Patent Office in EP Application No. 16911620.9.

* cited by examiner

ANALYSIS DATA PROCESSING METHOD AND ANALYSIS DATA PROCESSING DEVICE

CROSS REFERENCE TO RELATED APPLICATIONS

This application is a National Stage of International Application No. PCT/JP2016/072873 filed Aug. 3, 2016.

TECHNICAL FIELD

The present invention relates to an analysis data processing method and analysis data processing device for processing data collected with various types of analyzing devices, such as a liquid chromatographic analyzer or gas chromatographic analyzer as well as an infrared spectrophotometer, fluorescence X-ray analyzer or similar spectrum analyzer.

BACKGROUND ART

In a chromatographic analyzer in which a liquid chromatograph, gas chromatograph or similar type of component separation device is combined with a detector, a large number of components contained in a sample are temporally separated, and those components are individually detected with the detector, whereby analysis data (chromatogram data), which is a set of point data showing signal intensities within a specific period of time (retention time), is obtained. In the case of a chromatograph mass spectrometer (e.g. LC/MS or GC/MS) which employs a mass spectrometer (MS) as the detector, the components contained in a sample are temporally separated and individually subjected to a measurement with the mass spectrometer, whereby analysis data (chromatogram data or mass spectrum data), which is a set of point data showing signal intensifies at specific mass-to-charge ratios m/z and within a specific period of time, can be obtained.

In the case of a spectrum analyzer, such as an infrared spectrophotometer or fluorescent X-ray analyzer, a substance prepared as a sample is irradiated with light having a predetermined range of wavelengths, and a ray of light emitted from the irradiated substance is detected with a detector, whereby analysis data (spectrum data), which is a set of point data showing signal intensities at specific wavelengths (wavenumbers) or energy levels, is obtained. The number of point data forming those kinds of analysis data corresponds to the number of channels of the detector provided in the analyzer.

In any of those analyzing devices, a graph (chromatogram, mass spectrum or optical spectrum) can be created from the analysis data, with the horizontal axis indicating time, mass-to-charge ratio (m/z), wavelength or energy level, and the vertical axis indicating the output (signal intensity value) of each channel of the detector. On this graph, one or more peaks appear at specific positions (retention times, wavelengths/energy levels, or mass-to-charge ratios m/z) depending on the kinds of components contained in the sample. Accordingly, the kind of sample as well as the group which the sample belongs to can be identified by analytically processing analysis data obtained for a sample.

Let variable y (object variable) represent the content to be studied from analysis data collected with an analyzing device, i.e. the objective for which the analysis data are to be analytically processed, and also let variables $x_1$, $x_2$, $x_3$, . . . (explanatory variables) respectively represent outputs from the channels of the detector. Then, variable y can be expressed by using variables $x_1$, $x_2$, $x_3$ and so on. Since variables $x_1$, $x_2$, $x_3$, . . . are independent of each other, the analysis data mentioned earlier can statistically be handled as multidimensional data whose number of dimensions is equal to the number of variables $x_1$, $x_2$, $x_3$ and so on.

In the case of analysis data obtained for a sample containing a wide variety of compounds mixed together, a large number of peaks appear on a graph. Analyzing all peaks to determine their respective positions and magnitudes will lower the working efficiency. Paying attention to specific peaks, on the other hand, can certainly improve the working efficiency. However, it is difficult to determine which peaks are noteworthy. As analytical techniques for solving such a problem, multivariate analyses have been commonly used, such as the principal component analysis (PCA; Non-Patent Literature 1), nonnegative matrix factorization (NMF; Non-Patent Literature 2) or cluster analysis.

In a multivariate analysis, a plurality of sets of analysis data obtained for a plurality of groups of samples are compared with each other in terms of the position and/or shape of the peaks located on a graph. Based on the result of the comparison, unnecessary point data are deleted from the analysis data or integrated into other point data, to map the analysis data to lower dimensions. The analysis data mapped to lower dimensions are subsequently subjected to a regression analysis or discrimination analysis to create a model which expresses those analysis data.

A technique of linear regression analysis or linear discrimination analysis is applied in the case of comparatively simple data, such as two-dimensional data, three-dimensional data or similar type of data having a small number of explanatory variables. By comparison, in the case of multidimensional data, such as analysis data obtained with an analyzing device, it is difficult to apply the technique of linear regression or linear discrimination analysis. In such a case, the technique of non-linear regression analysis or non-linear discrimination analysis which employs a learning machine, such as a neural network or support vector machine (WM), is applied.

In the PCA or NW, analysis data are mapped to lower dimensions in such a manner that all dimensions in which the signal intensity significantly varies will be reflected in the eventually created model which expresses the analysis data.

For example, in the case of discriminating between different kinds of plastic based on a detection result obtained with a fluorescent X-ray analyzer, spectrum data are obtained beforehand for each of a plurality of known kinds of plastic, and a multivariate analysis is performed to compare the data between those kinds of plastic. A spectrum obtained for a specific kind of plastic includes not only the peaks originating from a material used as the base material for the plastic but also those originating from other additives, such as a coating material, plasticizer or flame retardant. Different kinds of plastic normally contain different kinds of additives. Therefore, the spectrum data obtained for different groups normally exhibit variations in not only the peaks originating from the base material but also those originating from additives. Accordingly, in the present case, the mapping of the analysis data to lower dimensions is performed so that both the peaks originating from the base material and those originating from additives will be reproduced in the lower dimensions.

As another example, in the case where a multivariate analysis using mass spectrum data obtained for biological samples collected from a group of healthy individuals and those obtained for biological samples collected from a group of cancer patients is performed to search for a pathological marker for a cancerous disease, a peak originating from a component different from the component serving as a pathological marker may also vary between the groups. A cause of such a variation is the lifestyle habits that are common to many cancer patients (smoking, drinking, etc.) i.e. a peak originating from a component associated with such lifestyle habits also significantly varies between the data of the healthy-individual group and those of the cancer-patient group. Accordingly, in the present case, the mapping of the analysis data to lower dimensions is performed so that the peaks originating from the components associated with the lifestyle habits will also be reproduced in the lower dimensions along with the peaks originating from the component serving as a pathological marker for the cancerous disease.

CITATION LIST

Non Patent Literature

Non-Patent Literature 1: "Tahenryou Kaiseki (Shuseihun Bunseki) Wo Katsuyou Shita Kuromatodeeta Kaiseki (Chromatographic data analysis using multivariate analysis (principal component analysis))", Shimadzu Corporation Website, [accessed on Jul. 25, 2016], the Internet Non-Patent Literature 2: NGOC-DIEP HO, "NON-NEGATIVE MATRIX FACTORIZATION ALGORITHMS AND APPLICATIONS", the Internet Non-Patent Literature 3: Tomoo AOYAMA and Hiroshi ICHIKAWA, "Obtaining the Correlation Indices between Drug Activity and Structural Parameters Using a Neural Network", Chem. Pharm. Bull. 39(2) 372-378, (1991)

Non-Patent Literature 4: Karen Simonyan et al., "Deep Inside Convolutional Networks: Visualising Image Classification Models and Saliency Maps", the Internet

SUMMARY OF INVENTION

Technical Problem

A problem as will be hereinafter described occurs if analysis data which have been mapped to lower dimensions as described earlier are inputted into a neural network, SVM or similar learning machine to create a model using the technique of non-linear regression analysis or non-linear discrimination analysis.

The peaks originating from additives or associated with lifestyle habits as described earlier do not represent the kind of plastic or characteristics of the cancerous disease; i.e., the magnitudes of such peaks have no causal relationship with the kind of plastic or the presence of a cancerous disease (the state of disease). In other words, there is no true correlation between them, and a correlation which is apparently present is a false correlation (spurious correlation). Therefore, in the case where analysis data acquired for a plurality of samples whose kinds of plastic or states of disease are previously known are used as training data for the modeling, if the training data apparently shows a correlation between a peak derived from additives and a specific kind of plastic, or between a peak originating from a component associated with the lifestyle habits and the state of disease, it is not always guaranteed that a similar correlation is also present in the analysis data which are the true target of the analysis. This leads to the so-called "overfitting", i.e. the state in which a technique which fits the training data does not suitably fit analysis data which are the true target of the analysis.

In order to prevent the overfitting, it is necessary to perform non-linear regression analysis or non-linear discrimination analysis using a wide variety of patterns of analysis data as the training data so that the peaks originating from the components which exhibit spurious correlations become as insignificant and ignorable as random noise. However, this requires an impractically large number of samples to be prepared.

Thus, in the area of the analytical processing of analysis data using statistical machine learning based on multidimensional analysis data collected with an analyzing device for a plurality of samples, the problem to be solved by the present invention is to provide a technique for excluding noise components from the analysis data while maintaining the dimensions which express characteristics of the sample.

Solution to Problem

A dimension which contributes to a regression analysis or discrimination analysis normally has a high degree of correlation with the output value of the function used for the regression analysis or discrimination analysis. This leads to the idea of deleting dimensions having unsatisfactory degrees of correlation and exclusively using dimensions having high degrees of correlation for the analysis. Needless to say, dimensions with no correlation are most likely to be noise components and should be deleted.

In the linear regression analysis or linear discrimination analysis, the correlation coefficient can be computationally determined. By comparison, in the regression analysis or discrimination analysis using a non-linear function using a neural network, support vector machine or similar machine learning, it is impossible to determine the correlation coefficient. However, in the regression/discrimination analysis using a neural network, the degree of contribution of each dimension of the input to the output can be calculated by partial differentiation (Non-Patent Literature 4). The method described in Non-Patent Literature 4 uses a sigmoid function in a non-linear discrimination/regression analysis employing a neural network, although the idea is not limited to the case of using a sigmoid function. Since most of the learning methods which use neural networks are categorized as the gradient method, it is possible to calculate a partial differential value (or partial subdifferential value) at each data point in the regression function or discrimination function. A regression or discrimination analysis by machine learning using a support vector machine similarly allows for the calculation of a partial differential value, or the calculation of a change in the output for a minimal change in the input as a value corresponding to the partial differential value, if both input and output of the machine learning have continuous values. As long as a partial differential value or a value which corresponds to the partial differential value at each data point can be calculated, it is possible to calculate the degree of contribution from that value.

Thus, the present invention provides a method for processing analysis data collected with an analyzing device for each of a plurality of samples, by applying an analytical technique using statistical machine learning to multidimensional analysis data formed by output values obtained from a plurality of channels of a multichannel detector provided in the analyzing device, the method including the steps of acquiring a non-linear regression function or non-linear discrimination function both of which expressing analysis data obtained for known samples;

calculating a contribution value based on a differential value of the non-linear regression function or non-linear discrimination function, the contribution value representing a degree to which each of the output values obtained from the plurality of channels forming the analysis data of the known samples contributes to the acquired non-linear regression function or non-linear discrimination function; and identifying one or more of the plurality of channels of the detector, which are to be used for processing analysis data obtained for an unknown sample, based on the contribution value.

In the previously described method for processing analysis data, the "analyzing device" may be any type of device having a multichannel detector. Representative examples include mass spectrometers, liquid chromatographic analyzers, gas chromatographic analyzers as well as infrared spectrophotometers, fluorescent X-ray analyzers and other types of spectrum analyzers.

One example of the "known samples" is samples which contain a known component or components. Another example is samples which belong to a known group, such as samples of a known kind of plastic or samples taken from either a cancer patient or healthy individual. Conversely, the "unknown sample" means a sample containing an unknown component or a sample Which belongs to an unknown group.

The "statistical machine learning" can performed using an appropriate type of learning machine, such as a neural network or support vector machine.

The differential value of the non-linear regression function or discrimination function expressing analysis data of known samples can be calculated by partially differentiating the regression function or discrimination function with respect to each of the variables (explanatory variables) which represent output values obtained from the channels of the detector. In order to reduce the amount of time required for the calculation, it is preferable to preprocess the analysis data by an appropriate operation, such as the extraction of a subset of the analysis data, division of the analysis data into clusters to perform calculations using data points which respectively represent the clusters, or calculation of the differential value for an empirically determined standard data pattern.

In the previously described method for processing analysis data, the criteria for identifying the selection of a channel based on the contribution value can be empirically set. As a representative criterion, n topmost channels may be selected in descending order of the contribution value.

In that case, the number n of the channels to be selected may preferably be determined so that no overfitting occurs.

The overfitting means a state in which a regression function or discrimination function fits the set of analysis data used for determining the regression function or discrimination function but does not fit other sets of analysis data. For example, the state of overfitting can be detected as follows: A set of analysis data obtained for known kinds of components is divided into training data for determining a regression function or discrimination function and test data for validating the regression function or discrimination function obtained for the training data. The precision is calculated for the case where the regression function or discrimination function obtained for the training data is applied to the same training data as well as for the case where the regression function or discrimination function is applied to the test data. The greater the difference in precision between the two cases is, the more likely the function is in the state of overfitting.

Accordingly, as a preferable mode the previously described method for processing analysis data, the method may further include the following steps: dividing analysis data obtained for known samples into training data and test data; tentatively selecting a channel to be used for processing analysis data obtained for an unknown sample, using the training data; calculating the precision for the case where the training data are processed using the tentatively selected channel as well as for the case where the test data are processed using the tentatively selected channel; and authorizing the use of the tentatively selected channel for the processing of the analysis data obtained for the unknown sample if the difference in precision between the training data and the test data is within a predetermined range.

In a preferable mode of the previously described method for processing analysis data, the method further includes: performing a weighting process in which a weight is determined for each of the plurality of channels forming the analysis data of known samples in accordance with the contribution value of each of the channels of the detector; and repeating the steps of recalculating the contribution value for each of the channels after the weighting process and updating the weight by the weighting process. Then, a channel to be used for the processing of analysis data obtained for an unknown sample is determined based on the weight or contribution value.

The weighting process may preferably be a process for emphasizing the degree of contribution, i.e. a process in which a greater contribution value is made to be even greater. For example, this can be achieved by calculating a power of the contribution value or taking the logarithm of the contribution value. The magnitude of the weight may be experimentally determined according to the kind of sample, type of analyzing device or other related factors. Regardless of whether such a weighting process is performed or the channels to be used are directly determined from the contribution value, the number of channels to be used may be gradually decreased by repeatedly performing the machine learning using the output values of the identified channels and the identification of the channels based on the result of the machine learning.

In the case where the result of the machine learning depends on the initial values of the coefficients to be determined by the machine learning, the contribution value is also affected by those initial values regardless of whether the channels are identified based on the contribution value before the weighting process or based on the contribution value after the weighting process. In such a case, the identification of the channels may be performed using the minimum value, maximum value or mean value of a plurality of contribution values, or a plurality of weights corresponding to these contribution values, obtained for a plurality of results of the machine learning performed a plurality of times. The authorization of the channels to be used may be performed based on how many times each channel has been selected in the machine learning performed a plurality of times.

Another aspect of the present invention is a data processing device for processing analysis data collected with an analyzing device for each of a plurality of samples, the data processing device configured to apply an analytical technique using statistical machine learning to multidimensional analysis data formed by output values obtained from a plurality of channels of a multichannel detector provided in the analyzing device, the data processing device including:

a) a function acquirer for acquiring a non-linear regression function or non-linear discrimination function, both of which expressing analysis data obtained for known samples;

b) a contribution calculator for calculating a contribution value based on a differential value of the non-linear regression function or non-linear discrimination function, the contribution value representing a degree to which each of the output values obtained from the plurality of channels forming the analysis data of the known samples contributes to the non-linear regression function or non-linear discrimination function acquired by the function acquirer; and c) a channel identifier for identifying one or more of the plurality of channels of the detector, which are to be used for processing analysis data obtained for an unknown sample, based on the contribution value.

Advantageous Effects of Invention

With the analysis data processing method and analysis data processing device according to the present invention, output values obtained from specific channels which will be noise components are excluded from output values obtained from a plurality of channels included in a set of analysis data, so as to analytically process analysis data for an unknown sample using the output values of specific channels which contribute to the regression analysis or discrimination analysis, i.e. output values of the channels which express characteristics of the sample.

DESCRIPTION OF EMBODIMENTS

Figure 1:
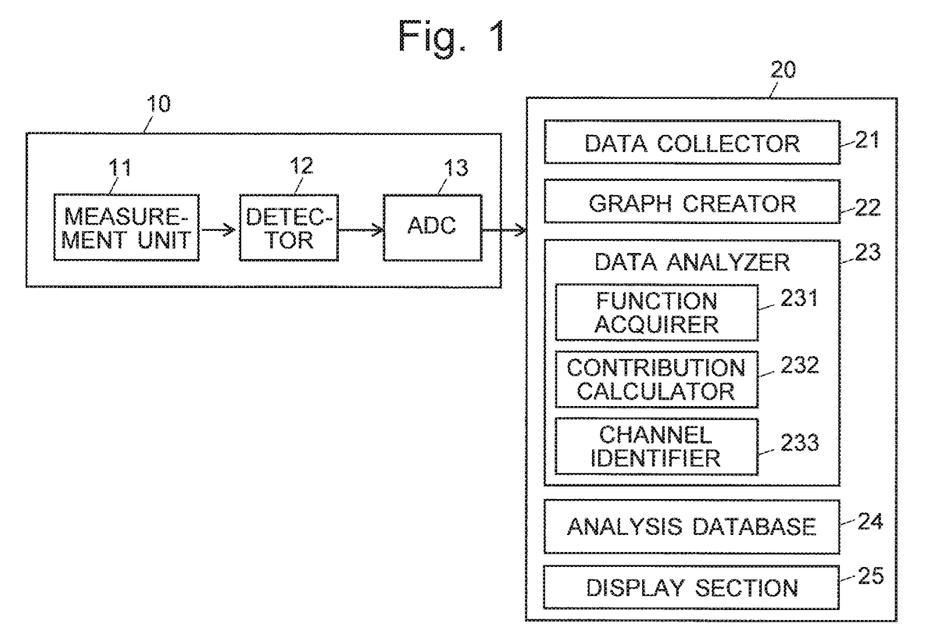
FIG. 1 is a schematic configuration diagram of an analyzing system as one embodiment of the present invention.

FIG. 1 is a schematic configuration diagram of an analyzing system as one embodiment of the present invention.

The analyzing system includes an analyzing device 10 and a data processing device 20. The analyzing device 10 includes a measurement unit 11, a multichannel detector 12 (which is hereinafter simply called the "detector" 12), and an analogue-to-digital converter (ADC) 13 for converting detection signals produced by the detector 12 into digital data. For example, if the analyzing device 10 is a Fourier transform infrared spectrophotometer (FTIR), the measurement unit 11 is an interferometer for generating a beam of interfering infrared light to be delivered onto a sample, while the detector 12 is a TGS detector, MCT detector or any appropriate type of detector.

The data processing device 20 includes: a data collector 21 for creating multidimensional analysis data by performing a predetermined data-processing operation on digital data obtained from output signals of the channels of the detector 12 by analogue-to-digital conversion in the ADC 13; a graph creator 22 for creating a graph, such as an infrared absorption spectrum or chromatogram, based on analysis data; a data analyzer 23 for analytically processing the analysis data; an analysis database 24 to be used for the analytical processing in the data analyzer 23; and a display section 25 for displaying the result of the analytical processing by the data analyzer 23.

Although the functions of the data processing device 20 may be realized by using dedicated hardware, they are normally realized by using a general-purpose personal computer as a hardware resource and executing, on this personal computer, dedicated data-processing software previously installed on the same computer.

Figure 2:
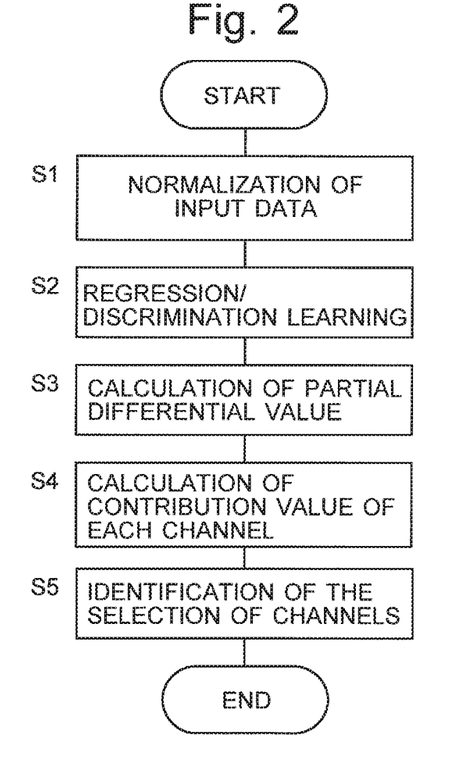
FIG. 2 is a flowchart showing the procedure of a data processing method.

The procedure of the data processing method in the data processing device 20 is hereinafter described with reference to the flowchart shown in FIG. 2, The processing in each step of the flowchart of FIG. 2 is carried out by the data analyzer 23 of the data processing device 20. It should be noted that the term "input data" in the following descriptions refers to the data entered into the data analyzer 23, while the term "output data" refers to the data produced by the data analyzer 23.

<Step 1: Normalization of Input Data>

Depending on the analyzing device 10, the reproducibility of the output values of the detector 12 may be low, in which case the output values of the detector 12 vary from measurement to measurement even if the same sample is analyzed. Furthermore, depending on the analyzing device 10, the sensitivity or signal-to-noise (SN) ratio of the detector 12 may vary from channel to channel. For example, in the case of a mass spectrometer, the detector normally has a low level of reproducibility, and the reproducibility of the peaks which appear on mass spectra is low. In the case of an absorption spectrometer, such as an FTIR, the sensitivity or SN ratio of the detector significantly varies depending on the wavelength.

Accordingly, the output values obtained from each channel of the detector 12 are normalized so that the amount of variation of those output values will have almost the same expected value on any channel of the detector 12, i.e. so that the output values will have the same standard deviation on any channel of the detector 12. Various commonly known methods can be used for this normalization. For example, output values obtained from a given channel and included a plurality of sets of analysis data, i.e. the values of a given peak in a plurality of optical spectra, mass spectra or chromatograms, may be individually divided by their standard deviation.

<Step 2: Non-Linear Regression Analysis or Non-Linear Discrimination Analysis Using Machine Learning>

Non-linear regression or non-linear discrimination (training) using a neural network, or similar learning machine is performed for a set of training data. The "training data" are analysis data obtained from the analyzing device 10 for samples for which the result of the analytical processing is previously known, such as samples of a known kind of resin or biological samples taken from a known type of subject which is either a cancer patient or healthy individual. This non-linear regression analysis or non-linear discrimination analysis of the training data is performed using the same set of regression variables or discrimination labels as will be used in the non-linear regression analysis or non-linear discrimination analysis of the analysis data obtained for the samples which are the true target of the analytical processing. A regression function or discrimination function expressing the training data is determined through the process of Step 2.

<Step 3: Calculation of Partial Differential Value of Input Data>

The regression function or discrimination function obtained for the training data is partially differentiated. For example, a technique as described in Non-Patent Literature 4 can be used for the partial differentiation. In this technique, an input value to a softmax function is regarded as the output value of the function which is partially differentiated.

<Step 4: Calculation of Contribution Value>

The contribution value of each channel is calculated using the partial differential values calculated in Step 3, For example, in the case of spectrum data obtained for identifying the kind of resin, a larger value of the signal intensity on a specific channel means a higher level of probability of the presence of a specific kind of substance. In such a case, since the partial differential values have positive values, a mean value of the partial differential values can be used as the contribution value. As another example, in the case of analyzing mass spectrum data to find a pathological marker that can be used for determining whether or not a subject is afflicted with a specific disease, the extent to which the signal value obtained from a specific channel is deviated from a proper value is important. In such a case, since the partial differential values can take both positive and negative values, the contribution value should be calculated from the quadratic norm of the partial differential values.

<Step 5: Determination of Channels>

A total of n channels are selected in descending order of the contribution value calculated in Step 4. A single value may be set for the number n of channels to be selected. However, it is preferable to set two or more values and perform, for each value of n, the regression or discrimination analysis in Step 2 for known test data (which are known analysis data different from the training data) using the output values obtained from the n channels selected. If the use of n channels for the regression or discrimination analysis causes neither serious overfitting nor significant deterioration in accuracy due to the decrease in the number of channels, those n channels can be designated as the channels to be eventually used for the data processing.

After the selection of then topmost channels, if the processing of Steps 2 through 4 is performed on the analysis data consisting of the output values obtained from those n channels, the ranking of the n channels in terms of the magnitude of the contribution value may change. To deal with this situation, a larger number (n+α) of channels than the n channels to be eventually selected may be initially selected, and the processing of Steps 2 through 5 may be performed on those selected channels to gradually decrease the number of channels and eventually determine the n channels to be used. This reduces the influence of the change in the ranking of the channels in terms of the contribution value.

The present invention has been applied to data processing for the discrimination between different kinds of resin based on a set of analysis data collected with an FTIR for plastic samples. The result of this data processing is hereinafter described with reference to FIGS. 3-7.

Figure 3:
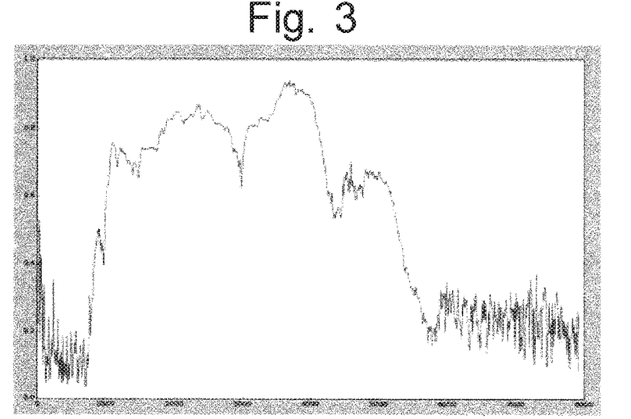
FIG. 3 is one example of an absorption-ratio spectrum obtained for a sample of polypropylene.
Figure 5:
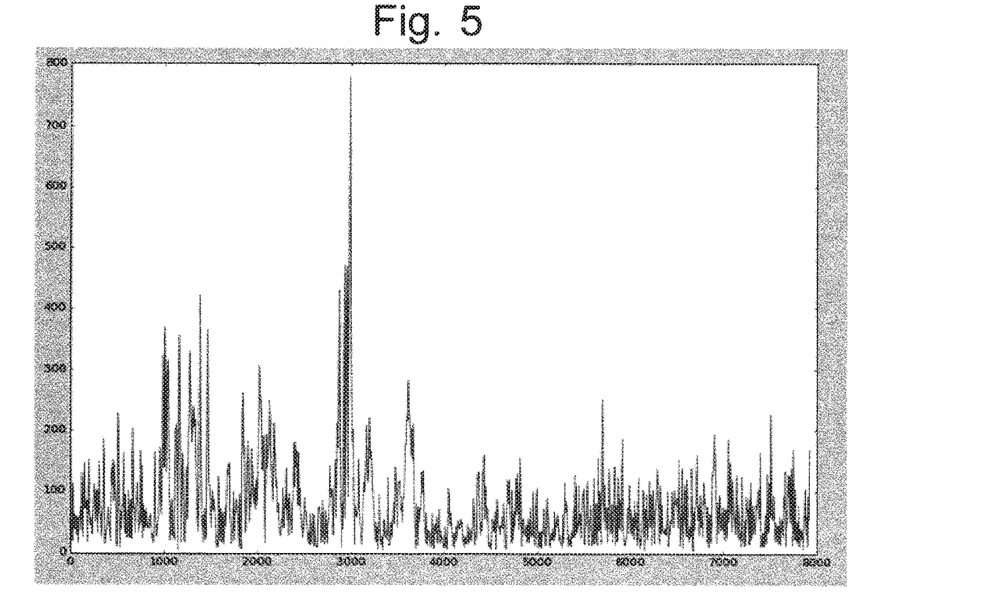
FIG. 5 is a diagram showing the contribution values of each data point in analysis data.
Figure 6:
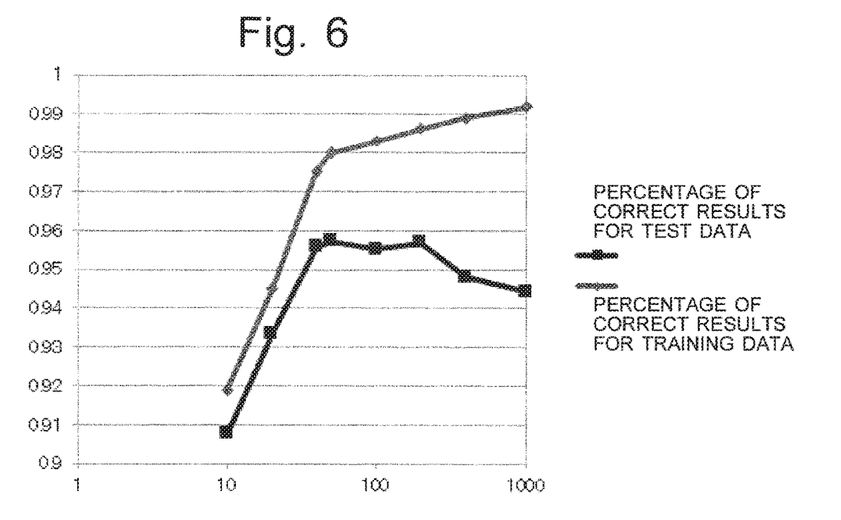
FIG. 6 is a graph showing a study result concerning an occurrence of overfitting.

FIGS. 3, 5, and 6 show the result of discrimination between PP and non-PP samples based on analysis data (spectrum data) obtained with the FTIR for four kinds of resins: polypropylene (PP) containing additives or other substances, polyethylene (PE), polyurethane resin (PUR), and acrylonitrile butadiene styrene copolymeric synthetic resin (ABS resin).

FIG. 3 shows one example of the absorption-ratio spectrum obtained for PP samples. This spectrum is a normalized version of an absorption-ratio spectrum obtained with the FTIR and was created by dividing the signal intensity value at each measurement point by the standard deviation of the signal intensity values at all measurement points. The absorption-ratio spectrum data normalized in this manner are sent to the function acquirer 231 in the data analyzer 23.

Figure 4:
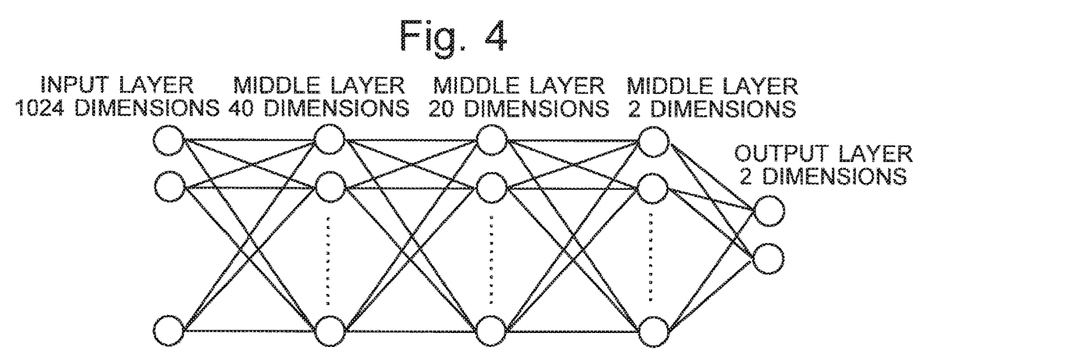
FIG. 4 is a conceptual diagram of a fully connected neural network.

In the data analyzer 23, a fully connected neural network as shown in FIG. 4 is used to discriminate between PP and non-PP resins. In the present example, an elu function is used as the activation function in the middle layers, while a softmax function is used as the activation function in the output layer. FIG. 5 shows the contribution values obtained as the result. In both FIGS. 3 and 5, the horizontal axis corresponds to the channels of the detector 12.

FIG. 6 shows the accuracy of the discrimination of the kind of resin using the training data and test data formed by the output values of the n topmost channels based on the obtained contribution values. The number of data points was 10000 in both cases.

Initially, the output values of all (1000) channels included in the analysis data were used to determine whether the sample was PP or non-PP. The accuracy was 94.1% for the test data and 99.2% for the training data, although these percentages also depend on the initial values used in the neural network. While a high accuracy was obtained for the training data, the accuracy became lower for the test data. This means that the overfitting occurred. From this state, the number of channels was gradually decreased. The percentage of correct discrimination for the training data gradually decreased with the decreasing number of channels, while the percentage of correct discrimination for the test data tended to increase and reached a peak when the number of channels was approximately 40. Thus, in the present experimental example, it is possible to prevent the overfilling and increase the percentage of correct discrimination (identification rate) by using the output values obtained from the channels ranked in the top 40 in terms of the contribution value.

Figure 7:
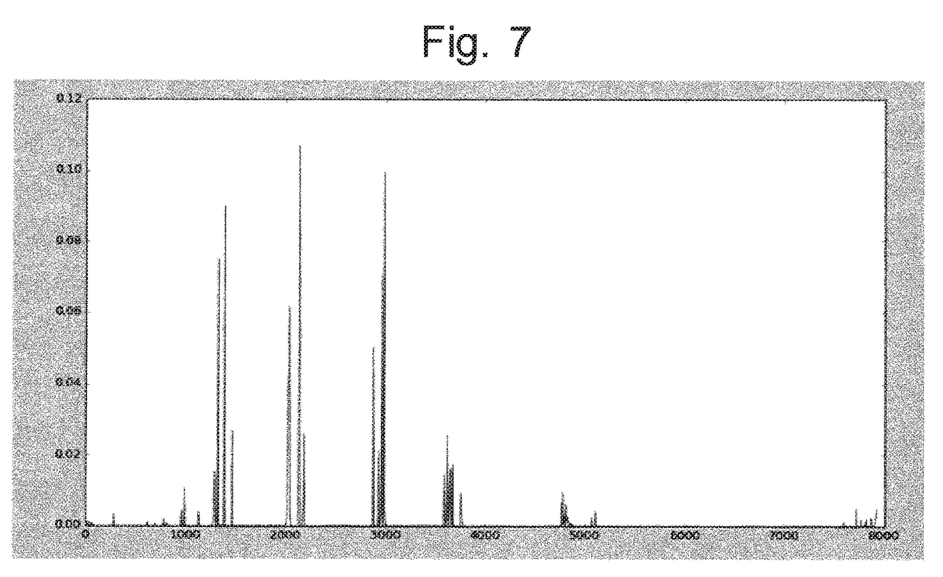
FIG. 7 is a diagram showing the contribution values after a weighting process.

FIG. 7 shows the result of the weighting process in which the normalization was carried out after an emphasizing process was performed on the contribution values shown in FIG. 5 by calculating the fourth power of each value of the contribution values. As can be seen in FIG. 7, the readability of the result is considerably improved by the weighting process. Based on the contribution values obtained through the weighting process, the discrimination test was once more performed using the analysis data consisting of the output values obtained from the top-40 channels. The percentage of correct discrimination was 95.5% for the test data and 96% for the training data. Thus, the overfitting was suppressed. This result demonstrates that the weighting process is effective for preventing the overfilling.

The present invention is not limited to the previously described embodiment but can be appropriately changed or modified.

For example, the normalization may be achieved by a commonly known technique in which a coefficient of variation (=standard deviation/mean value) calculated from the variation is used as the divisor.

In the previously described embodiment, the normalization for making the mean value be equal to 1 is performed after the emphasizing process for calculating the fourth power of the contribution value is carried out. The emphasizing process is closely related to the selection of the n topmost contribution values. The degree of emphasis (the value of the exponent) can be empirically regulated. A step function, sigmoid function or other commonly known non-linear monotonic functions may also be used for the emphasizing process in place of the calculation of a power of the contribution value.

REFERENCE SIGNS LIST

10 . . . Analyzing Device
11 . . . Measurement Unit
12 . . . Detector
13 . . . Analogue-To-Digital Converter (ADC)
20 . . . Data Processing Device
21 . . . Data Collector
22 . . . Graph Creator
23 . . . Data Analyzer
    231 . . . Function Acquirer
    232 . . . Contribution Calculator
    233 . . . Channel Identifier
24 . . . Analysis Database
25 . . . Display Section

The invention claimed is:

1. A method for analyzing an unknown sample, comprising:
collecting analysis data by an analyzing device for each of a plurality of samples, including known samples and the unknown sample, the analyzing device being a chromatographic or spectrum analyzer that includes a multichannel detector including a plurality of channels, and the analyzing device obtaining a first analysis data of the known samples and obtaining a second analysis data of the unknown sample, the method further comprising the steps of, by one or more computers:
acquiring a non-linear regression function or a non-linear discrimination function from the first analysis data of the known samples;
dividing the first analysis data into training data and test data;
training, a statistical machine learning model of contribution values based on a differential value of the non-linear regression function or the non-linear discrimination function to obtain a contribution value for each of the plurality of channels, the contribution value representing a degree at which each of output values obtained from the plurality of channels forming the first analysis data contributes to the acquired non-linear regression function or the acquired non-linear discrimination function, the training including tentatively selecting a channel to be used for processing the second analysis data by using the training data, and calculating a precision for a first case where the training data are processed using the tentatively selected channel as well as for a second case where the test data are processed using the tentatively selected channel;
identifying one or more of the plurality of channels having lowest contribution values, based on the contribution values for each of the plurality of channels obtained by the statistical machine learning model;
weighting each of the plurality of channels forming the first analysis data in accordance with the contribution value, and recalculating the contribution value for the plurality of weighted channels to update thereof; and
authorizing a use of the tentatively selected channel for processing the second analysis data if a difference in the precision between the first case and the second case is within a predetermined range, and analyzing the unknown sample by processing the second analysis data using one or more channels other than ones identified to have the lowest contribution values to identify the unknown sample, wherein the step of identifying one or more of the plurality of channels to be used for processing the second analysis data is performed after the step of recalculating the contribution value.

2. The method according to claim 1, further comprising the step of presenting information in regard to the one or more of the plurality of channels identified based on the contribution value.

3. A system for analyzing an unknown sample, comprising:
an analyzing device configured to collect analysis data for each of a plurality of samples including known samples and the unknown sample, the analyzing device being a chromatographic or spectrum analyzer that includes a multichannel detector including a plurality of channels, and the analyzing device obtaining a first analysis data of the known samples and obtaining a second analysis data of the unknown sample; and
a data processing device configured to process the analysis data collected with the analyzing device, the data processing device being a computer and configured to:
a) acquire a non-linear regression function or a non-linear discrimination function from the first analysis data of the known samples;
b) divide the first analysis data into training data and test data;
c) train a statistical machine learning model of contribution values based on a differential value of the non-linear regression function or the non-linear discrimination function to obtain a contribution value for each of the plurality of channels, the contribution value representing a degree at which each of output values obtained from the plurality of channels forming the first analysis data contributes to the acquired non-linear regression function or the acquired non-linear discrimination function, the training including tentatively selecting a channel to be used for processing the second analysis data by using the training data, and calculating a precision for a first case where the training data are processed using the tentatively selected channel as well as for a second case where the test data are processed using the tentatively selected channel;
d) identify one or more of the plurality of channels having lowest contribution values, based on the contribution values for each of the plurality of channels obtained by the statistical machine learning model;
e) weight each of the plurality of channels forming the first analysis data in accordance with the contribution value, and recalculate the contribution value for the plurality of weighted channels to update thereof; and
f) authorize a use of the tentatively selected channel for processing the second analysis data if a difference in the precision between the first case and the second case is within a predetermined range, and analyze the unknown sample by processing the second analysis data using the one or more channels other than ones identified to have the lowest contribution values to identify the unknown sample, wherein the step of identifying one or more of the plurality of channels to be used for processing the second analysis data is performed after the step of recalculating the contribution value.

4. The method according to claim 1, wherein the first analysis data and the second analysis data each include one or more peaks located on a graph.

5. The method according to claim 1, further comprising the step of displaying a result of analyzing the unknown sample on a display.

6. The method according to claim 1, further comprising the step of identifying one or more of the plurality of channels having highest contribution values, based on the contribution values for each of the plurality of channels obtained by the statistical machine learning model,
> wherein analyzing the unknown sample by processing the second analysis data includes using the one or more channels identified to have the highest contribution values.

7. The method according to claim 1, wherein each of the known samples is a sample in which components contained or a group to which it belongs is known.

8. The method according to claim 1, wherein the unknown sample is a sample in which components contained or a group to which it belongs is unknown.

9. The method according to claim 1, wherein to identify the unknown sample includes to determine a component contained in the unknown sample or determine a group to which the unknown sample belongs.

10. The system according to claim 3, wherein each of the known samples is a sample in which components contained or a group to which it belongs is known.

11. The system according to claim 3, wherein the unknown sample is a sample in which components contained or a group to which it belongs is unknown.

12. The system according to claim 3, wherein to identify the unknown sample includes to determine a component contained in the unknown sample or determine a group to which the unknown sample belongs.

\* \* \* \* \*